(12) United States Patent
Munger

(10) Patent No.: US 9,757,426 B2
(45) Date of Patent: Sep. 12, 2017

(54) PEPTIDE ADDITIVES FOR ENHANCING ACCEPTANCE AND INGESTION OF EDIBLES BY RODENTS AND USES THEREOF

(71) Applicant: UNIVERSITY OF MARYLAND, BALTIMORE, Baltimore, MD (US)

(72) Inventor: Steven D. Munger, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/768,357

(22) PCT Filed: Feb. 18, 2014

(86) PCT No.: PCT/US2014/016823
§ 371 (c)(1),
(2) Date: Aug. 17, 2015

(87) PCT Pub. No.: WO2014/127342
PCT Pub. Date: Aug. 21, 2014

(65) Prior Publication Data
US 2016/0000859 A1 Jan. 7, 2016

Related U.S. Application Data

(60) Provisional application No. 61/765,914, filed on Feb. 18, 2013.

(51) Int. Cl.
*A61K 38/10* (2006.01)
*A01N 35/00* (2006.01)
(Continued)

(52) U.S. Cl.
CPC ............ *A61K 38/10* (2013.01); *A01M 25/004* (2013.01); *A01N 25/004* (2013.01); *A01N 35/08* (2013.01); *A01N 63/00* (2013.01); *C07K 7/08* (2013.01)

(58) Field of Classification Search
CPC ........ A01N 35/08; A01N 63/00; A61K 38/10; C07K 7/08
See application file for complete search history.

(56) References Cited

U.S. PATENT DOCUMENTS 4,861,585 A * 8/1989 Galef, Jr. ............... A01N 59/02
424/84
8,349,328 B2 1/2013 Cayley et al.
(Continued)

FOREIGN PATENT DOCUMENTS

| FR | 2197514 | 3/1974 |
|---|---|---|
| WO | 88/02984 | 5/1988 |
| WO | 2006/095128 | 9/2006 |

OTHER PUBLICATIONS

Reeves et al. AIN-93 Purified Diets for Laboratory Rodents . . . The Journal of Nutrition. Nov. 1993, vol. 123, pp. 1939-1951.*
(Continued)

*Primary Examiner* — Jeffrey E Russel
(74) *Attorney, Agent, or Firm* — Wenderoth, Lind & Ponack, L.L.P.

(57) ABSTRACT

Methods of using of guanylin family peptides to induce food or odor preferences in mammals are provided, along with methods for inducing feeding responses in mammals, and methods of controlling pest populations of mammals, such as rodents.

28 Claims, 9 Drawing Sheets

(51) Int. Cl.
*A01N 35/08* (2006.01)
*A01N 63/00* (2006.01)
*C07K 7/08* (2006.01)
*A01M 25/00* (2006.01)
*A01N 25/00* (2006.01)

(56) References Cited

U.S. PATENT DOCUMENTS

2009/0110638 A1   4/2009   Koos
2010/0152118 A1*  6/2010   Shailubhai ............ A61K 38/10
                                                     514/1.1

OTHER PUBLICATIONS

Shailubhai et al. Uroguanylin Treatment Suppresses Polyp Formation in the ApcMin/+ Mouse . . . Cancer Research. Sep. 15, 2000, vol. 60, pp. 5151-5157.*
2018SX (Envigo)—Teklad Global 18% Protein Extruded Rodent Diet (Sterilizable). 2015.*
Munger, S. et al., An Olfactory Subsystem that Detects Carbon Disulfide and Mediates Food-Related Social Learning, Current Biology, 2010, vol. 20; pp. 1438-1444.
International Search Report for PCT/US2014/016823, dated Jun. 17, 2014.
Kelliher, Kevin R. et al., "Chemostimuli for guanylyl cyclase-D-expressing olfactory sensory neurons promote the acquisition of preferences for foods adulterated with the rodenticide warfarin", *Frontiers in Neuroscience*, 2015, vol. 9, Article 262, pp. 1-7.
Leinders-Zufall, Trese et al., "Contribution of the receptor guanylyl cyclase GC-D to chemosensory function in the olfactory epithelium", *PNAS*, 2007, vol. 104, No. 36, pp. 14507-14512.
Munger, Steven D. et al., "An Olfactory Subsystem that Detects Carbon Disulfide and Mediates Food-Related Social Learning", *Current Biology 20*, 2010, pp. 1438-1444.
Posadas-Andrews, Astrid et al., "Social Transmission of Food-Preferences in Adult Rats", *Animal Behaviour*, 1983, vol. 31, Issue 1, pp. 265-271.
Seeley, Randy J. et al., "Uroguanylin: how the gut got another satiety hormone", *J. Clinical Investigation*, 2011, vol. 121, No. 9, pp. 3384-3386.
Valentino, Michael A. et al., "A uroguanylin-GUCY2C endocrine axis regulates feeding in mice", *J. Clinical Investigation*, 2011, vol. 121, No. 9, pp. 3578-3588.
Valsecchi, Paola et al., "Social Influences on the Food Preferences of House Mice (*Mus musculus*)", *International Journal of Comparative Psychology*, 1989, vol. 2, No. 4, pp. 244-256.
Arakawa, Hiroyuki et al., "The Receptor Guanylyl Cyclase Type D (GC-D) Ligand Uroguanylin Promotes the Acquisition of Food Preferences in Mice" *Chem. Senses*, 2013, vol. 38, pp. 391-397.
Bean, N. Jay et al., "The Effect of Carbon Disulfide on Food Consumption by House Mice", *J. Wildlife Management*, 1988, vol. 52, No. 3, pp. 502-507.
Dobly, Alexandre et al., "Effect of Congeneric Chemical Signals of Different Ages on Foraging Response and Food Choice in the Field by Golden Spiny Mice (*Acomys russatus*)", *Journal of Chemical Ecology*, 2001, vol. 27, No. 10, pp. 1953-1961.
Forte Jr., Leonard Ralph, "Uroguanylin and guanylin peptides: pharmacology and experimental therapeutics", *Pharmacology & Therapeutics*, 2004, vol. 104, pp. 137-162.
Galef, Bennet G., "A case study in behavioral analysis, synthesis and attention to detail: Social learning of food preferences", *Behavioural Brain Research*, 2012, vol. 231, pp. 266-271.
Galef, Bennet G. et al, "Carbon disfulfide: A semiochemical mediating socially-induced diet choice in rats", *Physiology & Behavior*, 1988, vol. 42, pp. 119-124.
Evgenov et al.: "NO-independent stimulators and activators of soluble guanylate cyclase: discovery and therapeutic potential", Nature Reviews, 5(9): 755-768(2006).
Stowers et al.: "Olfactory mechanisms of stereotyped behavior: on the scent of specialized circuits", Current Opinion in Neurobiology, 20(3): 274-280(2010).
Zufall et al.: "Receptor guanylyl cyclases in mammalian olfactory function", Molecular and Cellular Biochemistry, 334(1-2):191-197(2009).
Extended European Search Report, issued Jul. 1, 2016 in corresponding European Application No. EP14752186.8.

* cited by examiner

SEQUENCE LISTING

```
<160> NUMBER OF SEQ ID NOS: 12

<210> SEQ ID NO 1
<211> LENGTH: 15
<212> TYPE: PRT
<213> ORGANISM: Mus musculus

<400> SEQUENCE: 1

Pro Asn Thr Cys Glu Ile Cys Ala Tyr Ala Ala Cys Thr Gly Cys
1               5                   10                  15

<210> SEQ ID NO 2
<211> LENGTH: 15
<212> TYPE: PRT
<213> ORGANISM: Canis familiaris

<400> SEQUENCE: 2

Pro Arg Ser Cys Glu Ile Cys Ala Phe Ala Ala Cys Ala Gly Cys
1               5                   10                  15

<210> SEQ ID NO 3
<211> LENGTH: 15
<212> TYPE: PRT
<213> ORGANISM: Felis catus

<400> SEQUENCE: 3

Pro Asp Ser Cys Glu Ile Cys Ala Phe Ala Ala Cys Ala Gly Cys
1               5                   10                  15

<210> SEQ ID NO 4
<211> LENGTH: 15
<212> TYPE: PRT
<213> ORGANISM: Equus caballus

<400> SEQUENCE: 4

Pro Arg Met Cys Glu Ile Cys Ala Phe Ala Ala Cys Ala Gly Cys
1               5                   10                  15

<210> SEQ ID NO 5
<211> LENGTH: 15
<212> TYPE: PRT
<213> ORGANISM: Bos primigenius

<400> SEQUENCE: 5

Pro Ser Thr Cys Glu Ile Cys Ala Tyr Ala Ala Cys Ala Gly Cys
1               5                   10                  15

<210> SEQ ID NO 6
<211> LENGTH: 15
<212> TYPE: PRT
```

```
<213> ORGANISM: Sus scrofa

<400> SEQUENCE: 6

Pro Ser Thr Cys Glu Ile Cys Ala Tyr Ala Ala Cys Ala Gly Cys
1               5                   10                  15

<210> SEQ ID NO 7
<211> LENGTH: 15
<212> TYPE: PRT
<213> ORGANISM: Mus musculus

<400> SEQUENCE: 7

Thr Asp Glu Cys Glu Leu Cys Ile Asn Val Ala Cys Thr Gly Cys
1               5                   10                  15

<210> SEQ ID NO 8
<211> LENGTH: 15
<212> TYPE: PRT
<213> ORGANISM: Canis familiaris

<400> SEQUENCE: 8

Ser Asp Asp Cys Glu Leu Cys Val Asn Val Ala Cys Thr Gly Cys
1               5                   10                  15

<210> SEQ ID NO 9
<211> LENGTH: 15
<212> TYPE: PRT
<213> ORGANISM: Felis catus

<400> SEQUENCE: 9

Asn Asp Asp Cys Glu Leu Cys Val Asn Val Ala Cys Thr Gly Cys
1               5                   10                  15

<210> SEQ ID NO 10
<211> LENGTH: 15
<212> TYPE: PRT
<213> ORGANISM: Equus caballus

<400> SEQUENCE: 10

Asn Asp Asp Cys Glu Leu Cys Val Asn Val Ala Cys Thr Gly Cys
1               5                   10                  15

<210> SEQ ID NO 11
<211> LENGTH: 16
<212> TYPE: PRT
<213> ORGANISM: Bos primigenius

<400> SEQUENCE: 11

Asn Asp Asp Cys Glu Leu Cys Val Asn Val Ala Cys Thr Gly Cys Ser
1               5                   10                  15

<210> SEQ ID NO 12
<211> LENGTH: 16
<212> TYPE: PRT
<213> ORGANISM: Sus scrofa

<400> SEQUENCE: 12

Gly Asp Asp Cys Glu Leu Cys Val Asn Val Ala Cys Thr Gly Cys Ser
1               5                   10                  15
```

PEPTIDE ADDITIVES FOR ENHANCING ACCEPTANCE AND INGESTION OF EDIBLES BY RODENTS AND USES THEREOF

STATEMENT OF FEDERALLY SPONSORED RESEARCH AND DEVELOPMENT

This invention was made with government support under Grant Number DC005633 awarded by National Institutes of Health. The government has certain rights in the invention.

BACKGROUND OF INVENTION

Social animals benefit from sharing information that promotes fitness and survival. For example, there is extensive evidence that rodents can transmit dietary preferences to neonates and to peer conspecifics via chemosensory cues (Galef 2012). In many cases, this transmission of food preferences requires active social investigation by naïve "observers" of "demonstrators" that have consumed particular foods. Rats and mice will acquire food preferences from the breath of live conspecifics but fail to acquire preferences to food odors presented on the hind quarters of the other animal (Galef 1985). In contrast, "observer" rats are able to form preferences when allowed to smell, but not contact, anesthetized demonstrator rats dusted with odored foods (Galef 1985). Therefore, the social transmission of food preference requires concurrent detection of both social odors (such as those present in the breath of the demonstrator animal) and odors from a particular food source (eaten by the demonstrator) (Galef et al. 1983; Posadas-Andrews and Roper 1983; Galef and Kennett 1987; Galef et al. 1988; Galef 2012).

Rodents also exhibit a preference for food sources that are in close proximity to conspecific social odors such as those present in soiled nest materials (Pastro and Banks 2006; Galef 2012). Rats consistently prefer to eat from a food marked by the excretory products of conspecifics than from an unmarked alternative (Galef and Heiber 1976; Laland and Plotkin 1991), with urine markings and the presence of fecal deposits around a food site rendering these food sites attractive (Laland and Plotkin 1993). Together, this suggests that rodents find such feeding environments to be beneficial for survival. These benefits could include information about the quantity or quality of nearby food even after conspecifics have vacated the area, and would thus offer a useful parallel to information transmitted via more direct social interactions.

There is strong experimental support for a role of the olfactory system in the detection of the social cues necessary for the formation of socially-transmitted food preferences (Galef 2012). Carbon disulfide ($CS_2$), an odorous component of rodent breath, can promote the acquisition of food preferences in both rats and mice when paired with a food odor (Bean et al. 1988; Galef et al. 1988; Munger et al. 2010). For example, rats will form food preferences when presented with cotton surrogates to which food odors and 1 ppm (13 µM) $CS_2$ has been added, but will exhibit no preference when the surrogate is supplemented with food odor alone (Galef et al. 1988). This concentration of $CS_2$ specifically activates a specialized subpopulation of olfactory sensory neurons (OSNs) in mice that express the receptor guanylyl cyclase isoform GC-D (Munger et al. 2010). Perturbation of the sensory transduction cascade in GC-D–expressing (GC-D+) OSNs, such as with the deletion of the gene encoding GC-D (Gucy2d), disrupts olfactory responses to $CS_2$ and prevents mice from acquiring socially transmitted food preferences (Munger et al. 2010).

The discovery of social cues that can be more easily utilized than components of rodent breath might aid in the development of effective means for controlling populations of pest rodents. The present invention is directed to this and other important goals.

BRIEF SUMMARY OF INVENTION

The present invention features methods for inducing a food or odor preference in a mammal, including rodents, such as a rat or a mouse. The methods are based on the findings presented herein that members of the guanylin family of peptides can induce the development of a food or odor preference in a rodent. The methods for inducing a food or odor preference in a mammal can be applied to such practical concerns as controlling a population of rodents, such as pest rodents in the wild. For example, a guanylin family peptide can be added to a training composition having an odor. When the training composition is introduced into the environment, the rodent smells and/or eats the composition, the rodent acquires a preference for the odor of the composition. An edible composition having the same odor, and supplemented with an additional compound such as a poison or contraceptive, can then be introduced in the same geographic location. The edible composition will be eaten by the rodents due to the established food or odor preference, even if the additional compound is detected by the rodent. Thus, the present invention can be used to control populations of pest rodents.

In a first embodiment, the invention is directed to a method for inducing a food or odor preference in a mammal, comprising exposing a mammal to a training composition comprising (i) matter having an odor and (ii) a guanylin family peptide or variant thereof, thereby inducing a food or odor preference in a mammal. In particular aspects of this embodiment, the mammal is a rodent, such as a rat or a mouse. In particular aspects of this embodiment, the guanylin family peptide is guanylin, uroguanylin or a variant thereof including, but not limited to, rat guanylin, rat uroguanylin, mouse guanylin, mouse uroguanylin, or a variant thereof. In a particular aspect of this embodiment, the training composition is a saline solution comprising (i) matter having an odor and (ii) between about 1 nM and 50 µM guanylin family peptide.

In a second embodiment, the invention is directed to a method for inducing a feeding response in a mammal, comprising (a) inducing a food or odor preference in a mammal by exposing a mammal to a training composition comprising (i) matter having an odor and (ii) a guanylin family peptide or variant thereof, and (b) providing the mammal with an edible composition comprising the odor of the training composition, thereby inducing a feeding response in a mammal. In particular aspects of this embodiment, the guanylin family peptide is guanylin, uroguanylin or a variant thereof including, but not limited to, rat guanylin, rat uroguanylin, mouse guanylin, mouse uroguanylin, or a variant thereof. In particular aspects of this embodiment, the edible composition is supplemented with one or more active agents, including, but not limited to, medications, contraceptives, or poisons. In a particular aspect of this embodiment, the training composition is a saline solution comprising (i) matter having an odor and (ii) between about 1 nM and 50 µM guanylin family peptide.

In a third embodiment, the invention is directed to a method for inducing a feeding response in a mammal, comprising providing a mammal with a complete composition comprising (i) an odor, (ii) a guanylin family peptide or variant thereof, and (iii) an edible composition, thereby inducing a feeding response in a mammal. In particular aspects of this embodiment, the complete composition comprises between about 1 nM and 50 µM guanylin family peptide. In particular aspects of this embodiment, the guanylin family peptide is guanylin, uroguanylin or a variant thereof including, but not limited to, rat guanylin, rat uroguanylin, mouse guanylin, mouse uroguanylin or a variant thereof. In particular aspects of this embodiment, the edible composition is supplemented with one or more active agents, including, but not limited to, medications, contraceptives, or poisons.

In a fourth embodiment, the invention is directed to a method for rodent control, comprising (a) inducing a food or odor preference in a rodent by exposing a rodent to a training composition comprising (i) matter having an odor, and (ii) a guanylin family peptide or variant thereof, and (b) administering to the rodent an edible composition comprising (i) the odor of the training composition and (ii) a rodent control agent, thereby controlling a rodent. In particular aspects of this embodiment, the rodent is a rat or mouse. In particular aspects of this embodiment, the rodent control agent is a poison and the control is death of the rodent. In a particular aspect of this embodiment, the training composition is a saline solution comprising (i) matter having an odor and (ii) between about 1 nM and 50 µM guanylin family peptide. In particular aspects of this embodiment, the guanylin family peptide is guanylin, uroguanylin or a variant thereof including, but not limited to, rat guanylin, rat uroguanylin, mouse guanylin, mouse uroguanylin, or a variant thereof. In particular aspects of this embodiment, the training composition and the edible composition are located in separate compartments of a bait station.

In a fifth embodiment, the invention is directed to a method for reducing a population of rodents, comprising (a) inducing a food or odor preference in a population of rodents by exposing a population of rodents to a training composition comprising (i) matter having an odor and (ii) a guanylin family peptide or variant thereof, and (b) administering to the population of rodents an edible composition comprising (i) the odor of the training composition and (ii) a rodent control agent, thereby reducing a population of rodents. In particular aspects of this embodiment, the rodent is a rat or mouse. In particular aspects of this embodiment, the rodent control agent is a poison and the control is death of the rodent. In a particular aspect of this embodiment, the training composition is a saline solution comprising (i) matter having an odor and (ii) between about 1 nM and 50 µM guanylin family peptide. In particular aspects of this embodiment, the guanylin family peptide is guanylin, uroguanylin or a variant thereof including, but not limited to, rat guanylin, rat uroguanylin, mouse guanylin, mouse uroguanylin, or a variant thereof. In particular aspects of this embodiment, the training composition and the edible composition are located in separate compartments of a bait station.

In a sixth embodiment, the invention is directed to a method for rodent control, comprising providing a complete composition to a rodent comprising (i) an odor, (ii) a guanylin family peptide or variant thereof, and (iii) an ingestible matter comprising a rodent control agent, thereby controlling a rodent. In particular aspects of this embodiment, the odor and the guanylin family peptide induce a food or odor preference in the rodent. In particular aspects of this embodiment, the rodent is a rat or mouse. In particular aspects of this embodiment, the rodent control agent is a poison and the control is death of the rodent. In particular aspects of this embodiment, the complete composition comprises between about 1 nM and 50 µM guanylin family peptide. In particular aspects of this embodiment, the guanylin family peptide is guanylin, uroguanylin or a variant thereof including, but not limited to, rat guanylin, rat uroguanylin, mouse guanylin, mouse uroguanylin, or a variant thereof.

In a seventh embodiment, the invention is directed to a method for reducing a population of rodents, comprising providing a complete composition to a population of rodents comprising (i) an odor, (ii) a guanylin family peptide or variant thereof, and (iii) an ingestible matter comprising a rodent control agent, thereby controlling a rodent. In particular aspects of this embodiment, the odor and the guanylin family peptide induce a food or odor preference in the rodent. In particular aspects of this embodiment, the rodent is a rat or mouse. In particular aspects of this embodiment, the rodent control agent is a poison and the control is death of the rodent. In particular aspects of this embodiment, the complete composition comprises between about 1 nM and 50 µM guanylin family peptide. In particular aspects of this embodiment, the guanylin family peptide is guanylin, uroguanylin or a variant thereof including, but not limited to, rat guanylin, rat uroguanylin, mouse guanylin, mouse uroguanylin, or a variant thereof.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

DETAILED DESCRIPTION OF THE INVENTION

I. Definitions

Figure 1:
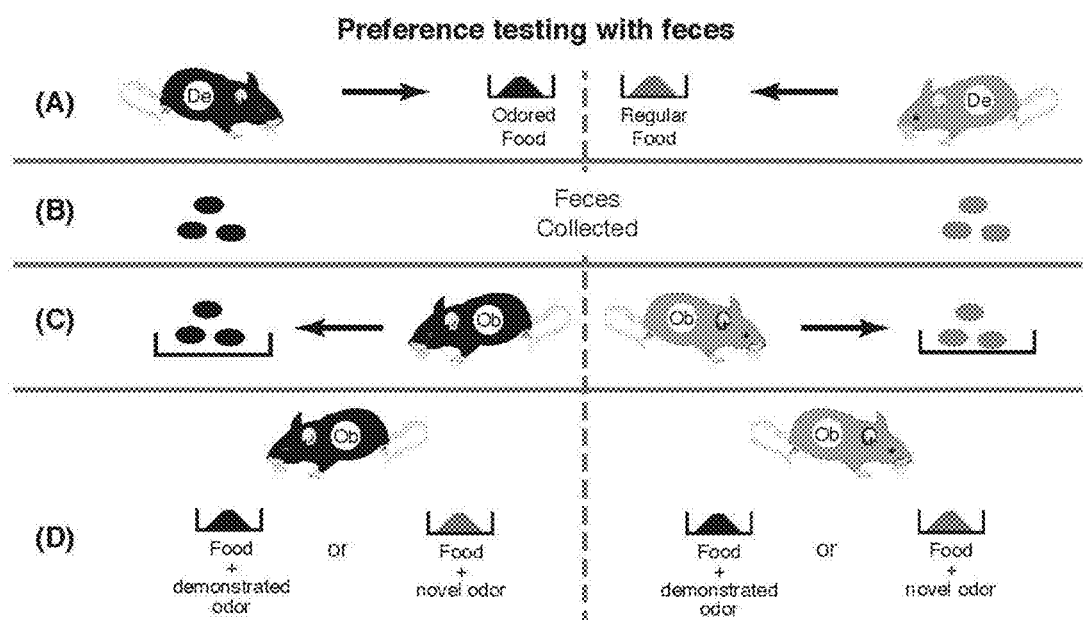
FIG. 1: Preference testing with feces. (A) C57BL/6J demonstrator (De) mice eat regular chow (gray) or chow with added odor (cocoa or cinnamon; black). (B) Feces are collected from each demonstrator mouse. (C) Observer (Ob) mice explore feces from the demonstrators. (D) Observer mice are then given the choice of two foods: one odored with cinnamon and one odored with cocoa.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Recent studies from Munger and colleagues have identified key neural substrates underlying the recognition of carbon disulfide and other select social odors, and the acquisition of food preferences (Munger et al. 2010; Leinders-Zufall et al. 2007). Carbon disulfide activates a specialized subpopulation of olfactory sensory neurons (OSNs) in the mouse nose. These OSNs are known as GC-D-expressing OSNs because they express a receptor guanylyl cyclase known as either GC-D or ONE-GC (product of the Gucy2d gene). Disruption of cellular signaling mechanisms in GC-D-expressing OSNs in living mice—either through targeted deletion of genes encoding key olfactory transduction proteins (e.g., GC-D or the cyclic nucleotide-gated channel subunit CNGA3) or pharmacological inhibition of these transduction pathways—results in inhibition of cellular responses to carbon disulfide. The same genetic or pharmacological modifications inhibit the acquisition of food preferences induced by social interaction or by olfactory detection of carbon disulfide, demonstrating the necessity of this olfactory cell subpopulation for the acquisition of the preference (Munger et al. 2010).

As shown herein, it has now been found that members of the guanylin family of peptides can promote the acquisition of food or odor preferences through the stimulation of GC-D-expressing OSNs in rodents. Guanylin and uroguanylin are guanylin family peptides that are naturally-occurring peptide hormones produced in the intestines and other tissues of many mammals, including rodents and humans.

The guanylin peptides are particularly intriguing candidates as social cues because they are excreted in urine and feces and are thus available for sampling by other animals (Forte 2004). Peptide concentration is linked to feeding, as intestinal secretion of the uroguanylin precursor prouroguanylin is upregulated after a meal and uroguanylin levels in urine are similarly increased postprandially (Forte 2004; Valentino et al. 2011). Guanylin family peptides offer potential advantages over volatile activators of GC-D-expressing OSNs such as carbon disulfide or putative gaseous activators such as carbonyl sulfide or carbon dioxide because peptides are generally more stable than volatiles or gases, suggesting longer dwell times at sites of application.

Guanylin family peptide members can vary in amino acid sequence within species (e.g., mouse guanylin and mouse uroguanylin differ) or between species (e.g., mouse uroguanylin and human uroguanylin differ), though as discussed below, all share some common motifs.

The present invention is generally directed to the use of guanylin family peptides in methods such as the induction of food or odor preferences in mammals, the induction of a feeding response in mammals, and more specifically, to methods of controlling pest populations of mammals, such as rodents.

As used herein, guanylin family peptides include guanylin, uroguanylin, and their analogues and variants, whether derived from natural sources or synthesized by chemical, biological or other means. Specific members of the family include, but are not limited to, the peptides provided in Table 1.

TABLE 1

Guanylin family peptides defined by single letter codes for amino acids.

Guanylin

| | |
|---|---|
| Rat/mouse | PNTCEICAYAACTGC (SEQ ID NO: 1) |
| Dog | PRSCEICAFAACAGC (SEQ ID NO: 2) |
| Cat | PDSCEICAFAACAGC (SEQ ID NO: 3) |
| Horse | PRMCEICAFAACAGC (SEQ ID NO: 4) |
| Cow | PSTCEICAYAACAGC (SEQ ID NO: 5) |
| Pig | PSTCEICAYAACAGC (SEQ ID NO: 6) |

Uroguanylin

| | |
|---|---|
| Rat/mouse | TDECELCINVACTGC (SEQ ID NO: 7) |
| Dog | SDDCELCVNVACTGC (SEQ ID NO: 8) |
| Cat | NDDCELCVNVACTGC (SEQ ID NO: 9) |
| Horse | NDDCELCVNVACTGC (SEQ ID NO: 10) |
| Cow | NDDCELCVNVACTGCS (SEQ ID NO: 11) |
| Pig | GDDCELCVNVACTGCS (SEQ ID NO: 12) |

Guanylin family peptides may include naturally occurring peptides isolated from animals (including from excretions, secretions, blood or other fluids or tissues) or chemically or biologically synthesized by standard techniques. The variants of guanylin and uroguanylin maintain the activity of the parent peptide. For example, the variants maintain the ability to activate GC-D-expressing OSNs. The variants have at least about 80, 81, 82, 83, 84, 85, 86, 87, 88, 89, 90, 91, 92, 93, 94, 95, 96, 97, 98 or 99% sequence identity over their entire length with the peptide on which they are based. The changes in sequence identity may be due to one or more of amino acid deletions, insertions and/or substitutions, where each substitution can be individually be a conservative or non-conservative amino acid substitution, using any amino acid, whether naturally-occurring, synthetic or otherwise altered to have specific attributes. As can be seen from Table 1, the guanylin peptides have one of two common amino acid motifs: ACTGC or ACAGC. The peptide variants of the present invention include variants having changes anywhere over the length of the peptide, variants having changes only in amino acids or regions of the peptide that are not in the common motifs, and variants having changes only in amino acids or regions of the peptide that are in the common motifs.

Method for Inducing a Food or Odor Preference in a Mammal

As discussed above, the invention is directed in a first embodiment to a method for inducing a food or odor preference in a mammal, comprising exposing a mammal to a training composition comprising (i) matter having an odor and (ii) a guanylin family peptide or variant thereof, thereby inducing a food or odor preference in a mammal.

This method is generally based on the concept that the mammal being trained to have a food or odor preference will encounter matter having an odor as well as a guanylin family peptide. Upon smelling the matter, both components of the odor and the guanylin family peptide will be taken up into the nose of the mammal, and different olfactory sensory neurons (OSNs) will be activated. As a result, a preference for the odor or a food having the odor will be induced in the mammal.

Method for Inducing a Feeding Response in a Mammal

As also discussed above, the invention is directed in a second embodiment to a method for inducing a feeding response in a mammal, comprising (a) inducing a food or odor preference in a mammal by exposing a mammal to a training composition comprising (i) matter having an odor and (ii) a guanylin family peptide or variant thereof, and (b) providing the mammal with an edible composition comprising the odor of the training composition, thereby inducing a feeding response in a mammal.

Such induction or conditioning can be used to induce a feeding response in an old, sick or malnourished mammal, for example, that might be resistant to ingest a foodstuff containing a medication or a high caloric value. Such mammals can first be conditioned to have a preference for a particular odor or a food having a particular odor using the training composition, and then found to readily ingest a food or liquid containing the same odor of the training composition. Thus, the edible composition is a selected food or liquid, optionally supplemented with one or more active agents, i.e., compounds that bring about a desired outcome in the mammal. The one or more other compounds are limited only in that they can be used in the edible composition, and include, for example, compounds having a positive effect on the mammal, such as a medication; compounds having a neutral effect on the mammal, such as a contraceptive; compounds having a negative effect on the mammal, such as a poison.

While this embodiment will typically be practiced using separate training and edible compositions, in a third embodiment the invention includes a method for inducing a feeding response in a mammal, comprising providing a mammal with a "complete composition" comprising (i) an odor, (ii) a guanylin family peptide or variant thereof, and (iii) an edible composition. The complete composition is provided to the mammal, and a food or odor preference is induced due to the presence of the odor and the guanylin family peptide in the composition. The mammal may consume the composition during the same encounter or instead consume the composition at a later time or in response to a future encounter with the composition. The odor of the complete composition can be an odor that is added to the composition or it can be the natural odor of the edible composition that is included in the complete composition. The edible composition is a selected food or liquid, optionally supplemented with one or more active agents, i.e., compounds that bring about a desired outcome in the mammal. The one or more other compounds are limited only in that they can be used in the edible composition, and include, for example, compounds having a positive effect on the mammal, such as a medication; compounds having a neutral effect on the mammal, such as a contraceptive; compounds having a negative effect on the mammal, such as a poison.

Method for Controlling a Selected Population of Mammals

As a practical application of the first and second embodiments of the invention, conditioning of mammals to have a preference for a particular odor or a food having a particular odor can be used in the control of the mammals. Such conditioning may reduce neophobia in a target population of pest rodents, for example, so that poison-laced baits (i.e., edible compositions) are consumed more quickly, reducing the time baits must be left out and reducing the possibility of bait ingestion by non-target species. The conditioning may also be used to increase the amount of bait ingested in individual feeding bouts so that ingested poisons reach lethal systemic levels in fewer feeding bouts. There is a need to increase the number of feeding bouts over time so that ingested poisons reach lethal systemic levels in fewer days.

Thus, in the fourth embodiment, the invention is directed to a method for rodent control, comprising (a) inducing a food or odor preference in a rodent by exposing a rodent to a training composition comprising (i) matter having an odor, and (ii) a guanylin family peptide or variant thereof, and (b) administering to the rodent an edible composition comprising (i) the odor of the training composition and (ii) a rodent control agent, thereby controlling a rodent.

In a fifth embodiment, the invention is directed to a method for reducing a population of rodents, comprising (a) inducing a food or odor preference in a population of rodents by exposing a population of rodents to a training composition comprising (i) matter having an odor and (ii) a guanylin family peptide or variant thereof, and (b) administering to the population of rodents an edible composition comprising (i) the odor of the training composition and (ii) a rodent control agent, thereby reducing a population of rodents.

Both of these methods are practiced by prior exposure of the mammal to a training composition comprising (i) matter having an odor and (ii) a guanylin family peptide, thereby inducing a food or odor preference in the mammal. Co-exposure of mammals to matter having a particular odor and one or more guanylin family peptides leads to the activation of GC-D-expressing OSNs in the mammal, and as demonstrated herein, a lasting preference for the selected odor.

In alternative aspects, the mammals can be exposed to a single composition, i.e., a "complete composition", that comprises (i) an odor, (ii) a guanylin family peptide, and (iii) an edible composition.

Thus, in a sixth embodiment, the invention is directed to a method for rodent control, comprising providing a complete composition to a rodent comprising (i) an odor, (ii) a guanylin family peptide or variant thereof, and (iii) an ingestible matter comprising a rodent control agent, thereby controlling a rodent. In a seventh embodiment, the invention is directed to a method for reducing a population of rodents, comprising providing a complete composition to a population of rodents comprising (i) an odor, (ii) a guanylin family peptide or variant thereof, and (iii) an ingestible matter comprising a rodent control agent, thereby controlling a rodent. The odor of the complete composition can be an odor that is added to the composition or it can be the natural odor of the edible composition that is included in the complete composition. The edible composition may be a selected food or liquid, or is may be supplemented to include one or more active agents, i.e., compounds that bring about a desired outcome in the mammal, such as a medication.

In each of the embodiments of the invention, "matter having an odor" is any matter than can be used to expose a mammal to an odor. As indicated above, the purpose of exposing a mammal to matter having an odor (and a guanylin family peptide) is to induce a food or odor preference in the mammal, where the food is scented by the selected odor. In this manner, the mammal can be trained to find certain foods to be acceptable because it will include the odor present in the matter to which it was trained. After a food or odor preference is induced in the mammal, and in the case of a pest rodent, it will ingest a bait exhibiting the odor regardless of whether it also includes a rodent control agent. Acceptable matter having an odor includes, but is not limited to, any matter that is ingestible or edible having a selected odor, a material soaked or impregnated with a particular odor, or a material to which a particular odor has been applied. Thus, the training composition need not be edible by the mammal per se, but need only be able to present a selected odor at the same time as a guanylin family peptide.

Matter that is ingestible or edible includes, but is not limited to, any item of food or type of liquid commonly consumed by the mammal, such as plant material (e.g., seeds; fruits; vegetables), animal materials (e.g. mammalian, fish or avian biomass; insects), and liquids such as water, saline solution or other non-toxic liquids commonly consumed by the mammal. However, matter ingestible by a mammal need not be a foodstuff or liquid and can be devoid of nutritional value.

A material soaked or impregnated with a particular odor, or a material to which a particular odor has been applied, can include, for example, a cotton ball can be sprayed or dusted with a particular substance that has an odor. The cotton ball is also processed to include a guanylin family peptide. As another example, a powder or microbeads can be formulated to contain or be coated with both components of an odor and guanylin family peptides. The powder or microbeads could be directly inhaled by the mammal into the nose (i.e., orthonasal delivery); or the powder or microbeads might coat the fur of a mammal and then subsequently be inhaled by a second mammal during grooming activities or other social interactions; or the powder or microbeads could be ingested and the powder or microbeads transported from the oral cavity to the nasal cavity via the oropharynx (i.e., retronasal delivery). As a further example, a rodent chow (i.e., a pelleted food available from pet store used as feed for pet rats or mice) can be sprayed or dusted with a guanylin family peptide. A rodent can be exposed to the treated chow and upon consuming some of the treated chow, it would be induced to develop a preference for the chow due to the activation of GC-D–expressing OSNs by the guanylin family peptide.

With respect to the odor itself, whether included in the training composition or the complete composition, it can be any odor that the target mammal can detect. While the odor will generally be an odor acceptable to the target mammal, due to the strength of the food or odor preference that can be induced, in certain aspects of the invention the odor can be one not normally acceptable to the mammal. The odor will typically be one that the species of mammal generally associates with a palatable food or liquid. However, the odor can also be one that the mammal has not previously encountered. Examples of useful odors include cinnamon, cocoa, oregano, and ginger. The amount of the odor or strength of the odor in the composition will depend on factors that include the species of target mammal, the identity of the odor, and the particular composition being used (i.e., the training composition or the complete composition). However, the skilled artisan will appreciate that due to the keen sense of smell exhibited by many mammals, the strength of the odor can be quite low in many cases.

Guanylin family peptides may be present in the training composition or the complete composition in a variety of formats, including in a liquid form, in a liquid-containing polymer matrices such as a gel, or in dehydrated form. Each training composition or complete composition may include a single guanylin family peptide isoform or a mixture of isoforms with different peptide sequences and olfactory efficacies.

The particular isoform of the guanylin family peptide that is included in the training composition or the complete composition may be varied, and when two more isoforms are included, they can be from the same or different species. Thus, the methods of the present invention include the use of training compositions and complete compositions comprising guanylin family peptides from the same species of mammal than is being induced to have a food or odor preference. The methods of the present invention also include the use of training compositions and complete compositions comprising guanylin family peptides from different species of mammal than is being induced to have a food or odor preference.

As used herein, "exposing" a mammal to a training composition or providing a mammal with the complete composition includes all means whereby the mammal will have sufficient exposure to the composition such that activation of GC-D–expressing OSNs occurs. Generally, such exposure will simply mean that the mammal is able to either smell or aspirate into the nose the composition by sniffing (orthonasal sampling) or ingest some of the composition (retronasal sampling). The length of time required for adequate exposure will vary based on a number of factors, include the identity of the composition (e.g., training or complete), the length of time between preparation of the composition and when the composition is encountered by the mammal, and the environmental conditions under which the composition is placed, to name a few. The exposure can be a single exposure, or it can be two, three, four, five or even more exposures. The time period separating the exposures when there are two or more can be minutes, hours, days, weeks or even months.

As provided in the third and fourth embodiments of the invention, the ability to induce a food or odor preference in a mammal has a number of practical applications.

In an important application, methods of inducing a food or odor preference in a rodent can be used as one step in means of controlling a rodent or reducing a population of rodents, such as a pest rodent or population of pest rodents in the wild. As provided in the third and fourth embodiments of the invention, such means include administering an edible composition comprising (i) the odor of the training composition and (ii) a rodent control agent to a rodent in which a food or odor preference has been induced.

The basis for these embodiments is the inclusion of the same odor of the training composition in the edible composition (i.e., bait) to make the edible composition appear familiar to the rodent due to the previously-induced food or odor preference. Thus, the rodent will prefer the edible composition to other available foods or liquids in the environment. The rodent will also be less likely to refuse the edible composition if the rodent detects the rodent control agent in the edible composition. As a result, the rodent will be more likely to consume the rodent control agent. The prior induction of food or odor preference may also allow baits to be consumed more quickly, reducing the time baits must be left out and reducing the possibility of bait ingestion by non-target species.

Alternative means for achieving the same goals are provided in the fifth and sixth embodiments of the invention where a single, complete composition is used that comprises (i) an odor, (ii) a guanylin family peptide, and (iii) an ingestible matter comprising a rodent control agent, in place of separate training and edible compositions.

The rodent control agents that may be included in the compositions of the present invention include any agent that can be used to control a rodent or a population of rodents. Examples include, but are not limited to, agents that impair, inhibit or stop the growth of a rodent, agents that induce the death of a rodent, and agents that prevent the rodent from reproducing, such as a contraceptive agent or sterilizing agent, to name only a few. The skilled artisan will understand that the identity of the agent is only limited in that it must maintain its activity when used in the compositions and that it must be able to exert its activity upon ingestion by a rodent. Acceptable agents include acute and chronic rodenticides, and other toxic substances or their precursors, such as, but not limited to, anticoagulants, metal phosphides, hypercalcaemia agents and other chemical poisons; contraceptive compounds; compounds causing sterility.

"Acute rodenticides" include, but are not limited to, zinc phosphide, trizinc phosphide, norbomide, red squill (active ingredient scilliroside), sodium (mono) fluoroacetate, fluoroacetamide, alphachloralose, ANTU, and thallium sulphate. As well, some rodenticidal chemicals, such as caliciferol, bromethalin and flupropadine may be described as sub-acute rodenticides in that a lethal dose is ingested in the first 24 hours. Although acute rodenticides are not as effective as the chronic ones, they can be validly used in emergency situations, such as when the rat population must be destroyed in a short period of time. However, they have many disadvantages, which include high toxicity for humans and non-target species, along with increasing the rodents' suspiciousness.

"Chronic rodenticides" include, but are not limited to, agents that act as anti-coagulants, including but not limited to the first generation anticoagulants hydroxycoumarins (e.g. warfarin, coumachlor, coumafuryl, coumatetralyl) and indane-diones (e.g. pindone, diphacinone, chlorphacinone, pivaldione); and the second generation anti-coagulants (single dose) bromadiolone, brodifacoum, difenacoum, flocoumafen, and difethialone.

Suitable formulations of the compositions that may be used include, but are not limited to, flaked baits, pellets, paraffinized baits, track or contact powders, gels, fats, and pastes. By "flaked bait" is meant flaked and pulverized bait composed of a mixture of flaked cereals and crumbled and pulverized grains and other highly attractive food components. The components used are: flaked wheat and oats enriched with baiting substances, sugar, whole wheat, sunflower seeds. The presence of different components increases the possibility the target animal will detect a particularly appreciated one among them and eat it.

By "pellets" is meant pellets produced starting with pulverization of cereals. Afterwards, the cereals powder and the active ingredient are mixed together with thickening substances and animal and vegetable proteins, and then the mixture is drawn. The palatability of the baits is comparable to whole cereals, although the pellets are harder in texture and have more uniform diffusion of the rodent control agent in the bait with respect to the whole cereals. The pellets hardness satisfies the mice and rats' need for gnawing.

By "paraffinized baits" is meant compounds in which the rodent control agent and other ingredients are mixed with paraffin. These formulations have been developed with the intent of limiting the perishability of the rodent control agent, especially in environments with a high degree of humidity. However, these formulations have low palatability. The paraffinized bait can be obtained, according to a conventional technology, by mixing the melted paraffin with other ingredients, then casting the mixture into molds, where it hardens. However, it has been noted that the high paraffin content (up to 50%), extensive heating to which the ingredients were subjected, and their non-homogeneous distribution in the bait, significantly reduce its palatability. Two alternative formulation techniques can be used, which allow paraffinized baits to be obtained with good palatability: the compression technique (ovules) and the extrusion technique, which makes blocks which can be fixed in the poisoning stations, preventing the rodents from removing the blocks easily. The paraffinized baits, cannot be extracted with water and have the disadvantage of liquefying due to exposure to natural light, which disperses the rodent control agent in the environment when it rains.

By "track or contact powders" is meant track or contact powders conceived to be placed on the rodents' habitual paths or blown into their holes. The rodent, once covered with the powder, undoubtedly tries to clean itself using the tongue and thereby they consume the active ingredient. Although the powders are extremely effective in controlling the rodents, currently the system is scarcely used due to high risk of environmental contamination.

By "gel baits or fat baits" are meant baits having gel formulation or fat baits with good palatability and of high quality that cannot be transferred by the rodents. Moreover, they remain fresh for a long time. In some cases, the fresh gel bait or fat bait can make use of the same mechanism as the powder, whereby the rat, trying to clean its hair with the tongue, swallows the rodent control agent. Liquid concentrate compounds are indicated for bait production and are mixed with attractive substances, which can vary according to the food habits of the mice and/or rats population to be fought. The liquid contains coloring agents (blue, green, red) to give color to the baits.

By "paste baits" is meant (fresh bait or fresh paste) a preparation in the form of paste, having powdery consistence, amalgamated with animal and vegetable fats, and to which antioxidant substances are added to prevent it from becoming rancid. These baits are packaged in packets of filter paper that makes their positioning easy. The paste bait contains ingredients that provide optimal palatability for rodents in many situations, especially when only dry food is available. Packaging in filters or packets allows a baiting diffusion of the odors and attractant substances contained therein. The paste bait has the disadvantage of not always ensuring adequate disinfesting action, since the rodent control agent is not consistently contained therein in a quantity high enough to achieve the lethal effect on the mouse/rat.

The compositions may include one or more of the following additives: (i) flavorants—a flavor component selected from chocolate, dried powdered crustacean, yeast, feces, fish meal, meat, berries and mixtures of two or more of these; (ii) preservatives against fungi, yeasts, bacteria and the like, including but not limited to, sorbic acid and bronopol; (iii) bittering substances such as denatonium benzoate to prevent accidental ingestion by a non-target species; (iv) emulsifying agents such as triethanolamine (TEA); (v) pigments and/or coloring agents to highlight the rodenticidal bait, preferably pigments which create a blue color; one or more sugars (carbohydrates) such as saccharose, lactose and the like to increase the palatability of the bait; (vi) the guanylin family peptide that was included in the training composition or a different guanylin family peptide.

Training compositions comprising guanylin family peptides may be presented at the same time as the edible composition where the method to be practice is one of rodent control or reducing a population of rodents using separate compositions. As an example, a bait station can be prepared that includes the training composition in one compartment and the edible composition in another. The training compositions may also be presented to a mammal hours, days, weeks or perhaps months prior to exposure to the edible composition. The training composition and the edible composition may be provided in the same geographic location or different locations, whether they are provided at the same point in time or provided at different points in time.

As used herein, "administering" the edible composition to the rodent or population of rodents simply means placing the edible composition in such a location and under such circumstances that the rodent or rodents can easily encounter and ingest the edible composition. The term is not limited in scope to physically feeding rodents by hand, as might be done in a laboratory setting. Similarly, "providing" the complete composition to the rodent or population of rodents simply means placing the complete composition in such a location and under such circumstances that the rodent or rodents can easily encounter the composition.

In each of the embodiments of the invention, reference to a mammal includes all mammalian species, including, but not limited to, rodents such as mice and rats, dogs, cats, cattle, pigs, sheep, goats, and horses.

In each of the embodiments of the invention, reference to a rodent includes all members of the order Rodentia, such as, but not limited to, scaly-tailed squirrels, springhares, beavers, gophers, kangaroo rats, kangaroo mice, Laotian rock rats, gundis, African mole rats, Old World porcupines, dassie rats, cane rats, giant hutias, chinchilla rats, hutias, Guinea pigs, capybaras, chinchillas, viscachas, tuco-tucos, agoutis, pacas, pacaranas, spiny rats, New World porcupines, nutrias, coypus, octodonts, jerboas, jumping mice, mouse-like hamsters, hamsters, New World rats, New World mice, muskrats, voles, true mice, true rats, gerbils, spiny mice, crested rats, climbing mice, rock mice, white-tailed rats, Malagasy rats and mice, spiny dormice, mole rats, bamboo rats, zokors, mountain beavers, squirrels, chipmunks, prairie dogs, and marmots.

III. Formulations and Doses

As should be evident to the skilled artisan, the amount of guanylin family peptides to be included in a composition, whether it is a training composition, an edible composition or a complete composition, will vary widely depending on such factors as the identity of the components of the composition, the environmental conditions into which the composition will be placed, and the target rodent species, to name a few. However, when the composition is a liquid or a gel, it has been found that a concentration of between about 1 pM and 1 mM guanylin family peptide is suitable. In certain aspects, between about 100 pM and 100 µM is suitable. In other aspects, between about 100 pM and 1 µM, between about 1 nM and 50 µM or between about 0.1 nM and 100 nM is suitable. When the composition is a solid, a concentration of between about 1 pM and 1 mM guanylin family peptide is suitable. In certain aspects, between about 100 pM and 100 µM is suitable. In other aspects, between about 100 pM and 1 µM, between about 1 nM and 50 µM or between about 0.1 nM and 100 nM is suitable.

IV. Examples

Animals—All experimental procedures were approved by the University of Maryland School of Medicine Institutional Animal Care and Use Committee. Mice were housed in an AAALAC accredited laboratory facility. Male C57BL/6J (B6) mice were obtained from the Jackson Laboratory (Bar Harbor, Minn.). Gucy2d $^{-/31}$ and Gucy2d$^{-/-}$ mice, which have been described previously (Leinders-Zufall et al. 2007; Munger et al. 2010), were maintained in the breeding colony. Mice were group-housed (3-4 per cage) in standard cages (28 cm×17 cm×12.5 cm) with filter-top lids. All mice received water and standard rodent chow ad libitum. The room in which the mice resided was environmentally controlled on a 12:12 h light:dark cycle (0600-1800 hr lighting) at a temperature of 21° C., relative humidity of 50-60%.

Food preference testing—Food preference assays were modified from those used previously for testing the social transmission of food preference in rats and mice (Galef et al. 1983; Posadas-Andrews and Roper 1983; Valsecchi and Galef 1989; Crawley 2007; Ryan et al. 2008; Munger et al. 2010). In all experiments, subject mice were pair-housed for four days in standard cages with the food container placed on the cage floor. Mice were fed a crushed rodent diet (2018SX, Harlan) to habituate them to powdered food. The amount of food was restricted to 2 g/mouse/day to facilitate feeding during the food preference tests. Food preference was quantified by computing the ratio of the demonstrated food consumed versus the total food consumed by the subject mice (Preference ratio, PR=demonstrated food consumed/total food consumed). All data were expressed as mean ±S.E.M. Differences were accepted as significant if $p<0.05$ (see below for statistical tests).

Preference testing after feces exposure—A schematic of the experimental design is presented in FIG. 1. B6 mice were randomly assigned as demonstrator or observer mice. Demonstrator mice (n=16) were pair-housed for five days and supplied either unadulterated powdered chow or powdered chow adulterated with either cocoa powder (2%, Hershey Co.) or cinnamon (1%, McCormick & Co.). Fecal pellets deposited in the demonstrators' home cages were collected (0.5-1.0 gram) just prior to testing of the observer mice. These fecal pellets were placed in a clean petri dish (3.5 cm) in a new cage. Individual observer mice were then placed in the cages and allowed to explore for 1 hr. Each observer mouse was then moved to a clean cage. After 3 hrs, observer mice were presented with two food trays (3.5 cm petri dishes mounted to a weighted plastic stage), one of which contained cocoa-odored food (3.5 g) and the other cinnamon-odored food (3.5 g). Subject mice were allowed to feed for 1 hr, at which point the food trays were removed and weighed to calculate the amount of each food consumed. Z tests [where z=(mean observed PR—0.50)/standard error of the mean] were performed to determine if there was a statistically significant preference for the demonstrated food (a PR of 0.5 indicates no preference). Significance between stimulus conditions was determined by one-way ANOVA.

Figure 2:
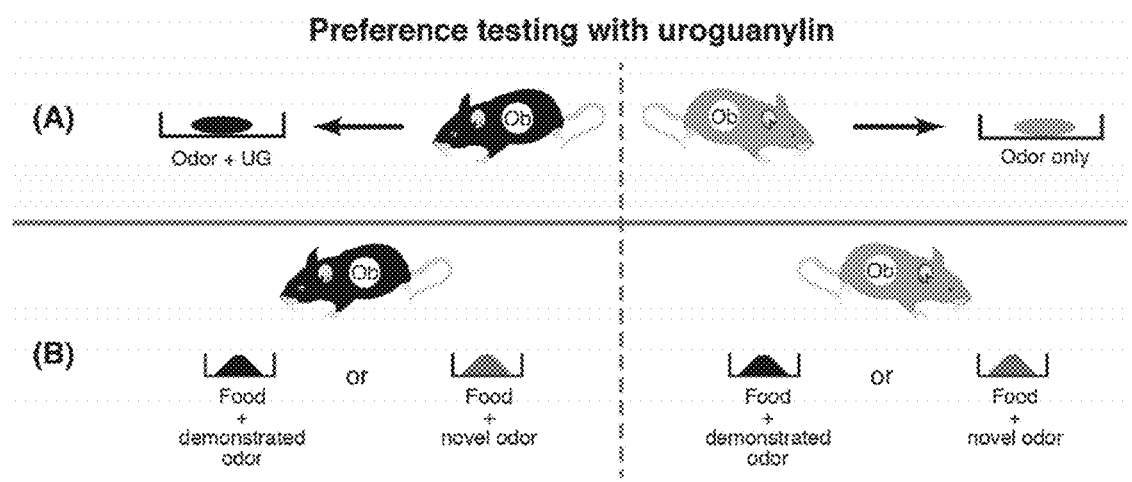
FIG. 2: Preference testing with uroguanylin. (A) Observer (Ob) mice (either C57BL/6J or Gucy2d$^{+/-}$ and $-/-$) explore saline containing a food odor (cocoa or cinnamon) and 50 µM or 50 nM uroguanylin (UG; black) or the food odor alone (gray). (B) Observer mice are then given the choice of two foods: one odored with cinnamon and one odored with cocoa.

Preference testing after uroguanylin exposure—A schematic of the experimental design is presented in FIG. 2. B6 mice were randomly assigned into one of three groups (n=8 each). On the test day, each mouse was moved to individual cages and presented with a petri dish containing a drop of saline (150 μl) with added flavor powder (2% cocoa or 1% cinnamon) with or without uroguanylin (0, 50 nM or 50 μM). After 1 hr exposure, mice were moved to clean cages. After 3 hrs, mice were presented with two food trays (3.5 cm petri dishes mounted to a weighted plastic stage), one of which contained cocoa-odored food (3.5 g) and the other cinnamon-odored food (3.5 g). Subject mice were allowed to feed for 1 hr, at which point the food trays were removed and weighed to calculate the amount of each food consumed. Z tests were performed to determine if there was a statistically significant preference for the demonstrated food. Significance between stimulus conditions was determined by one-way ANOVA.

This experimental paradigm was then used to test the contribution of GC-D to uroguanylin-dependent acquisition of food preferences (FIG. 2). Gucy2d$^{+/-}$ and Gucy2d$^{-/-}$ mice (n=16 each) were each assigned either of two groups. Previous studies demonstrated that Gucy2d$^{+/-}$ mice are phenotypically identical to wildtype in their physiological responses to olfactory stimuli (including uroguanylin) and in their ability to acquire socially transmitted food preferences. On the test day, each mouse was moved to an individual cage and presented with a petri dish containing a drop of saline (150 μl) with added flavor powder (2% cocoa or 1% cinnamon) and uroguanylin (50 nM or 50 μM). After 1 hr exposure, subject mice were moved to clean cages. After 3 hrs, subject mice were presented with two food trays (3.5 cm petri dishes mounted to a weighted plastic stage), one of which contained cocoa-odored food (3.5 g) and the other cinnamon-odored food (3.5 g). Subject mice were allowed to feed for 1 hr, at which point the food trays were removed and weighed to calculate the amount of each food consumed. Z tests were performed to determine if there was a statistically significant preference for the demonstrated food. Significance between stimulus conditions, between genotype, and for the interaction between stimulus conditions and genotype was determined by two-way ANOVA.

Figure 3:
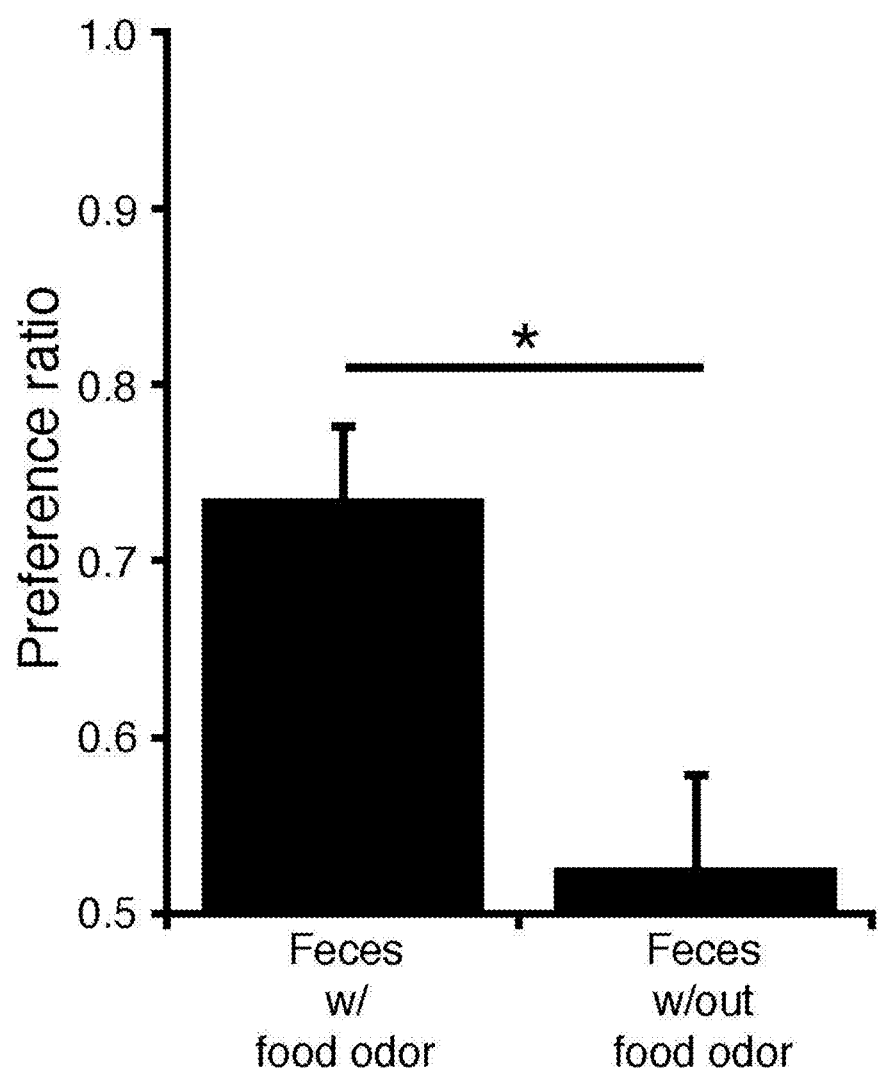
FIG. 3: Feces contain chemostimuli that promote the acquisition of food preferences. C57BL/6J mice exposed to feces obtained from mice that consumed odored (cinnamon or cocoa) show a significant preference (preference ratio=demonstrated food consumed/total food consumed) for food containing that same odor (Z test, z=5.74, p=0.02). Mice exposed to feces obtained from mice that consumed food with no added odor showed no preference for cinnamon- or cocoa-odored food.

The experimental conditions and methodology described above were used to determine whether mice can acquire food preferences through interactions with feces of conspecifics. Rodents prefer to feed in locations where conspecifics have deposited urine and feces (Galef and Heiber 1976; Laland and Plotkin 1991; 1993). Observer mice were introduced to a food odor through exploration of fecal pellets obtained from a demonstrator mouse that had consumed plain chow or odored chow (containing either 2% cocoa or 1% cinnamon (w/w)). Observer mice were then presented with a choice of two powdered chows: one containing cocoa and one containing cinnamon. Observer mice (n=8) exposed to feces from demonstrators that consumed food without added cocoa or cinnamon showed no preference for either cocoa or cinnamon-odored food (FIG. 3, Table 2; PR, 0.53±0.05; Z test, z=0.50, p=0.44; *: one-way ANOVA F(1,14)=8.61, p<0.05; error bars, s.e.m.). By contrast, mice (n=8) exposed to feces from demonstrators that consumed odored food showed a strong preference for the food containing that same odor (FIG. 3, Table 2; PR, 0.74±0.04). These data indicate that feces, like breath, contain social cues that can promote the acquisition of food preferences.

Figure 4:
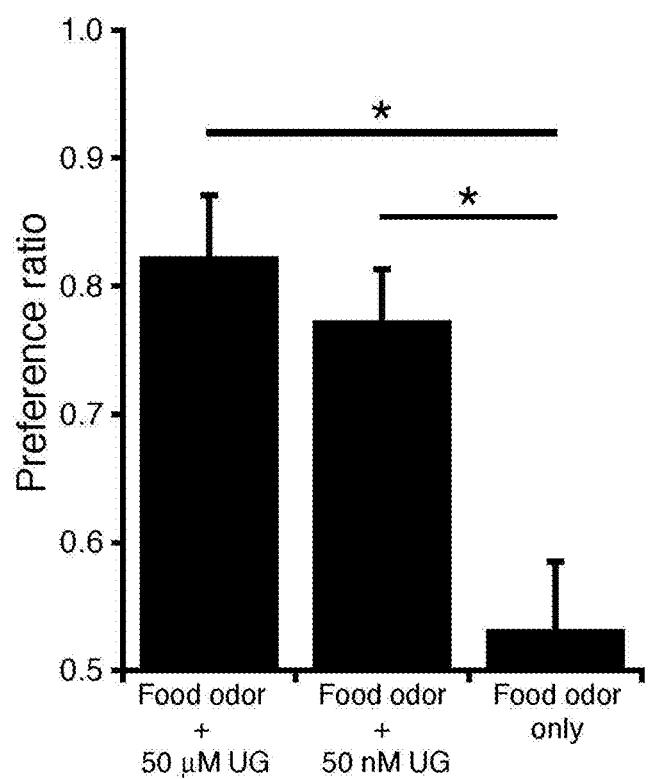
FIG. 4: Uroguanylin promotes the acquisition of food preferences. C57BL/6J mice exposed to a food odor (cinnamon or cocoa) plus uroguanylin show a significant preference (preference ratio=demonstrated food consumed/total food consumed) for food containing that same odor (50 nM uroguanylin: Z test, z=6.87, p=0.008; 50 µM uroguanylin: Z test, z=6.72, p=0.009). Mice exposed to the food odor alone showed no preference for cinnamon- or cocoa-odored food.

The chemostimulus $CS_2$, when paired with a food odor, is sufficient to increase the attractiveness of foods and to promote the acquisition of food preferences in mice (Bean et al. 1988; Munger et al. 2010). Whether uroguanylin could serve a similar role was tested. Individual observer mice were allowed to interact with a petri dish containing an odor (2% cocoa or 1% cinnamon) with or without uroguanylin (50 nM or 50 μM) in saline. Each mouse was subsequently presented with a choice of two odored chows (cocoa vs. cinnamon). Observer mice exposed to odored saline without uroguanylin (n=8) showed no preference for cocoa- or cinnamon-odored food (FIG. 4, Table 2; PR, 0.53±0.05; Z test, z=0.61, p=0.41; one-way ANOVA: F(2,21)=9.491, p<0.01; *: Dunnett post-hoc, p<0.01; error bars, s.e.m.). However, mice exposed to saline containing either concentration of uroguanylin (n=8 each) showed a strong preference for food containing the demonstrated odor (FIG. 4, Table 2; 50 nM uroguanylin: PR, 0.77±0.04; 50 μM uroguanylin: PR, 0.82±0.05). Together, these results show that uroguanylin, a component of both feces and urine, can promote the acquisition of food preferences.

Figure 5:
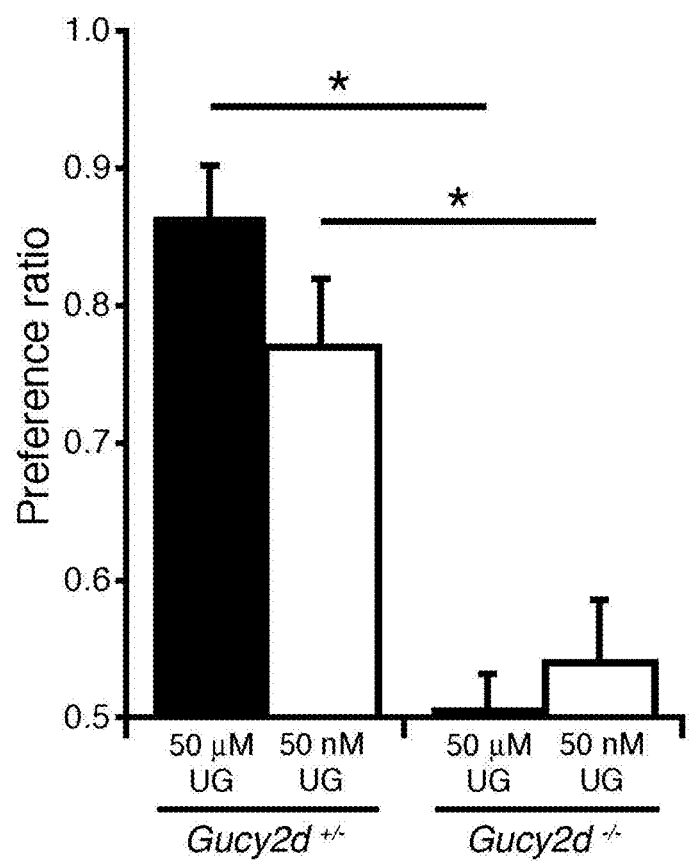
FIG. 5: GC-D is required for the acquisition of food preferences in response to uroguanylin. Gucy2d$^{+/-}$ mice exposed to a food odor (cinnamon or cocoa) plus uroguanylin show a significant preference (preference ratio=demonstrated food consumed/total food consumed) for food containing that same odor (50 nM uroguanylin: Z test, z=5.40, p=0.03; 50 µM uroguanylin: Z test, z=9.47, p=0.0004). Gucy2d$^{-/-}$ mice exposed to a food odor (cinnamon or cocoa) plus uroguanylin showed no preference for cinnamon- or cocoa-odored food (50 nM uroguanylin: Z test, z=0.94, p=0.37; 50 µM uroguanylin: Z test, z=0.27, p=0.46).

Finally, it was asked whether GC-D+ OSNs mediate uroguanylin-dependent acquisition of food preferences. It was predicted to be the case as GC-D+ OSNs are sensitive detectors of uroguanylin and mediate the acquisition of food preferences in response to interactions with both live demonstrators and $CS_2$ (Leinders-Zufall et al. 2007; Munger et al. 2010). The ability of Gucy2d$^{-/-}$ mice (which do not produce GC-D) or their heterozygous controls to acquire food preferences after exposure to a food odor (cocoa or cinnamon) was assessed in the presence of either 50 nM or 50 µM uroguanylin. Similar to B6 mice, Gucy2d$^{+/-}$ mice (n=8 each group) exhibited a strong preference for food containing the demonstrated odor (FIG. 5, Table 2; 50 nM uroguanylin: PR, 0.77±0.05; 50 µM uroguanylin: PR, 0.86±0.04). However, Gucy2d$^{-/-}$ mice (n=8 each group) showed no preference for either the demonstrated or novel odor (FIG. 5, Table 2; 50 nM uroguanylin: PR, 0.54±0.04; 50 µM uroguanylin: PR, 0.51±0.03). Two-way ANOVA: uroguanylin concentration, F(1,28)=0.47, p=0.42; *, genotype, F(1,28)=45.57, p<0.0001; uroguanylin concentration× genotype, F(1,28)=2.23, p=0.09. Error bars, s.e.m. Thus, GC-D, and the OSNs that express it, is required for the acquisition of uroguanylin-dependent food preferences.

TABLE 2

Amount of food consumed (g) by observer mice in food preference assays (mean ± s.e.m.).

| Stimulus | Mice | | |
|---|---|---|---|
| (food consumed) | C57BL/6J | Gucy2d$^{+/-}$ | Gucy2d$^{+/-}$ |
| Feces (w/odor) | | | |
| Total food | 2.22 ± 0.25 | | |
| w/demonstrated odor | 1.64 ± 0.21 | | |
| w/novel odor | 0.58 ± 0.10 | | |
| Feces (w/o odor) | | | |
| Total food | 1.30 ± 0.11 | | |
| w/cocoa | 0.61 ± 0.09 | | |
| w/cinnamon | 0.68 ± 0.09 | | |
| Odor alone | | | |
| Total food | 0.94 ± 0.13 | | |
| w/demonstrated odor | 0.49 ± 0.09 | | |
| w/novel odor | 0.45 ± 0.09 | | |
| Odor + UG (50 µM) | | | |
| Total food | 1.50 ± 0.26 | 1.61 ± 0.16 | 0.89 ± 0.17 |
| w/demonstrated odor | 1.15 ± 0.14 | 1.39 ± 0.15 | 0.45 ± 0.09 |
| w/novel odor | 0.35 ± 0.12 | 0.22 ± 0.07 | 0.44 ± 0.08 |
| Odor + UG (50 nM) | | | |
| Total food | 1.42 ± 0.19 | 1.78 ± 0.34 | 1.13 ± 0.22 |
| w/demonstrated odor | 1.08 ± 0.14 | 1.60 ± 0.27 | 0.65 ± 0.15 |
| w/novel odor | 0.34 ± 0.08 | 0.50 ± 0.11 | 0.49 ± 0.09 |

UG: uroguanylin;
Odor: either 2% cocoa or 1% cinnamon (counterbalanced)

Figure 6:
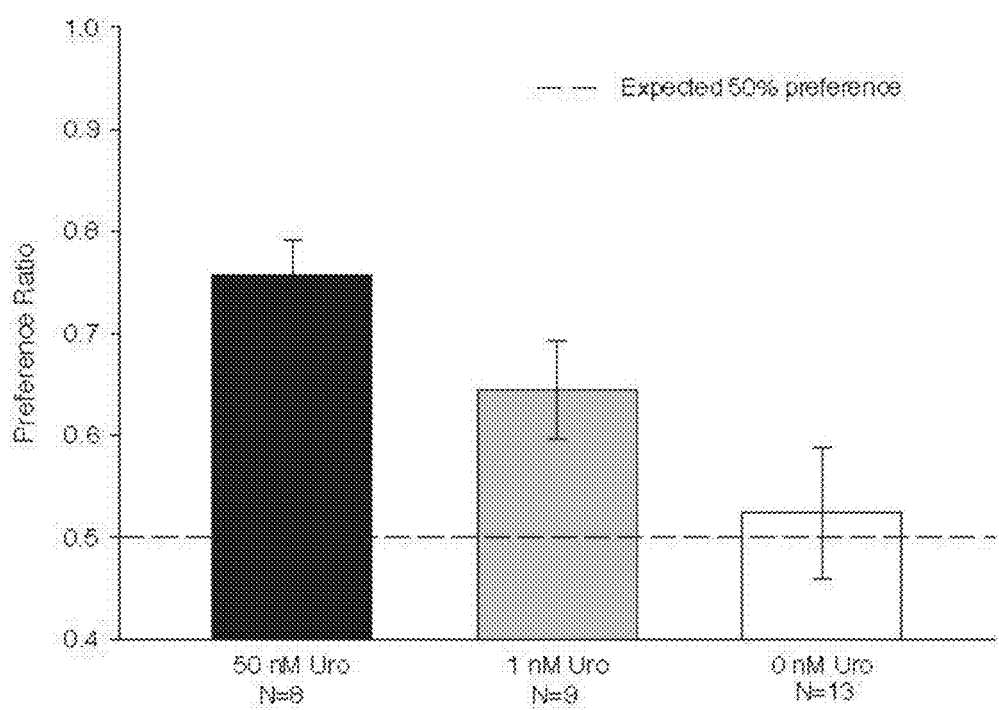
FIG. 6: Concentration/response functions for uroguanylin. Mice formed preferences for warfarin-containing food with the demonstrated odor when the food odor was demonstrated with 50 nM uroguanylin (PR=0.76 +/−0.04 SEM) and 1 nM uroguanylin (PR=0.65 +/−0.05 SEM) but not in the absence of uroguanylin (PR=0.52 +/−0.06 SEM).

Concentration/response functions were studies for uroguanylin. Mice were allowed to explore saline containing uroguanylin (0, 1 or 50 nM) with a food odor (demonstrated odor) for 1 hr. Mice were then given a choice of two powdered foods containing 0.025% warfarin plus either the demonstrated odor or a novel odor. The preference ratio (PR) is computed as: food with demonstrated odor (g) consumed/ total food (g) consumed. A preference ratio of 0.5 indicates no preference. Mice formed preferences for warfarin-containing food with the demonstrated odor when the food odor was demonstrated with 50 nM uroguanylin (PR=0.76 +/−0.04 SEM) and 1 nM uroguanylin (PR=0.65 +/−0.05 SEM) but not in the absence of uroguanylin (PR=0.52 +/− 0.06 SEM) (FIG. 6). Statistical analysis with a one-way ANOVA revealed a significant effect of uroguanylin concentration (F [1,29]=4.31, P<0.05). Tukey's post hoc analysis showed that PR exhibited by animals exposed to 50 nM uroguanylin were significantly greater than controls (0 nM uroguanylin; P<0.05). The PR for 1 nM uroguanylin was not significantly different from either 50 nM or 0 nM uroguanylin (P>0.05).

Figure 7:
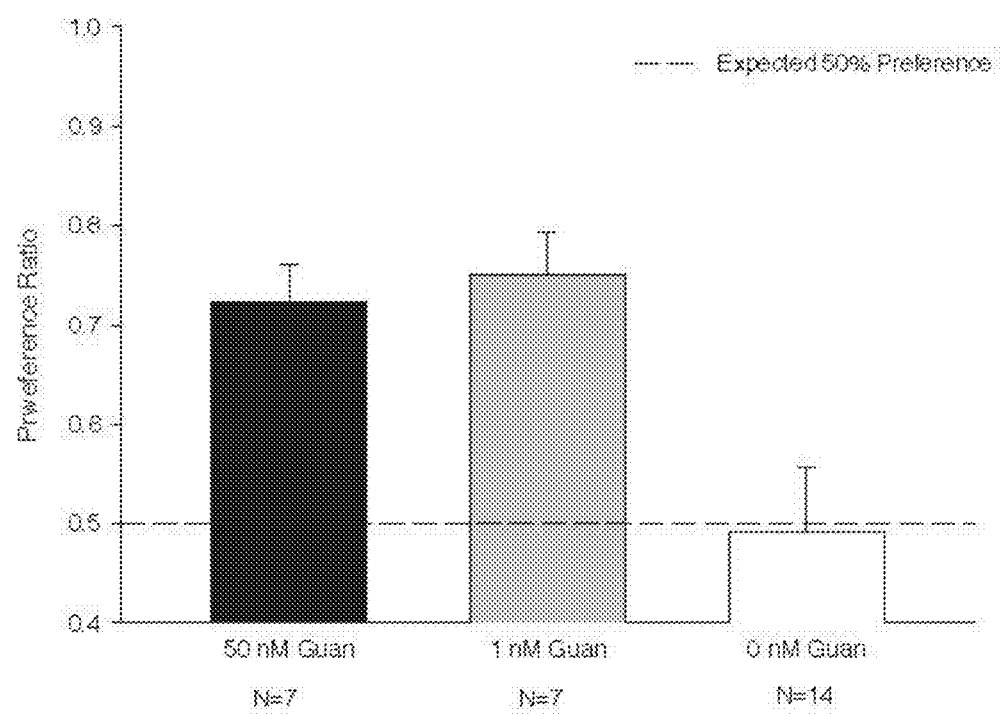
FIG. 7: Concentration/response functions for guanylin. Mice formed preferences for warfarin-containing food with the demonstrated odor when the food odor was demonstrated with 50 nM guanylin (PR=0.72 +/−0.04 SEM) or 1 nM guanylin (PR=0.75 +/−0.04 SEM) but not in the absence of guanylin (PR=0.49 +/−0.06 SEM).

Concentration/response functions were also studied for guanylin. Mice were allowed to explore saline containing guanylin (0, 1 or 50 nM) with a food odor (demonstrated odor) for 1 hr. Mice were then given a choice of two powdered foods containing 0.025% warfarin plus either the demonstrated odor or a novel odor. The preference ratio (PR) is computed as: food with demonstrated odor (g) consumed/total food (g) consumed. A preference ratio of 0.5 indicates no preference. Mice formed preferences for warfarin-containing food with the demonstrated odor when the food odor was demonstrated with 50 nM guanylin (PR=0.72 +/−0.04 SEM) or 1 nM guanylin (PR=0.75 +/−0.04 SEM) but not in the absence of guanylin (PR=0.49 +/−0.06 SEM) (FIG. 7). Statistical analysis with a one-way ANOVA revealed a significant effect of guanylin concentration (F [1,26]=6.29, P<0.01). Tukey's post hoc analysis showed that preferences formed with 50 nM guanylin or 1 nM guanylin were both significantly greater than 0 nM guanylin (P<0.05).

Figure 8:
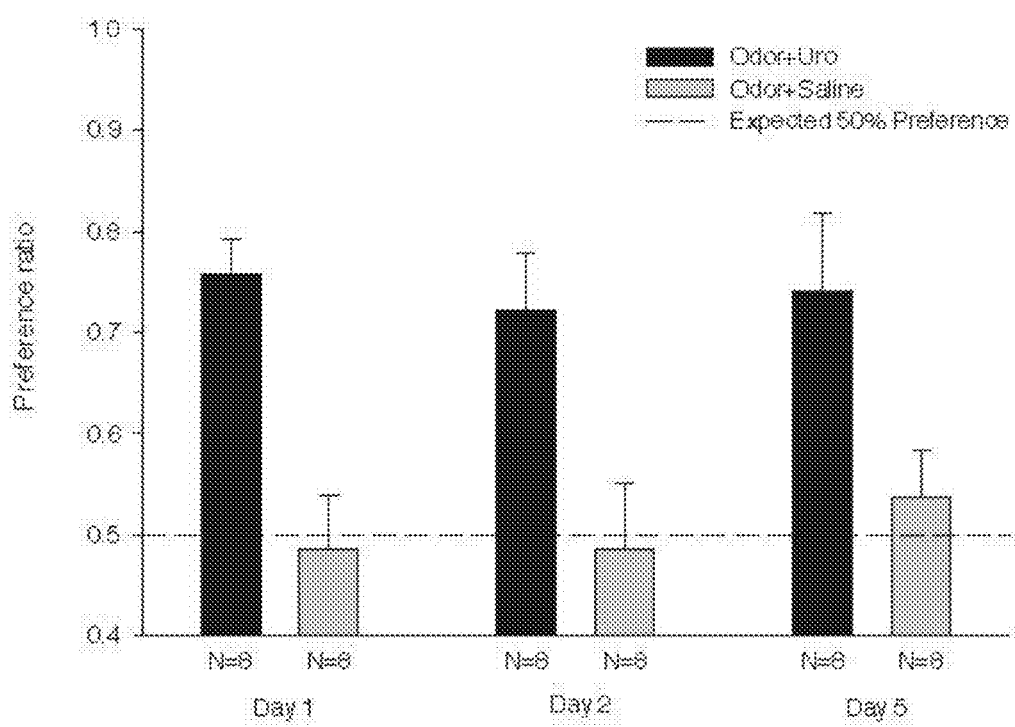
FIG. 8: Uroguanylin-dependent preferences were maintained. Mice that had sampled the food odor with 50 nM uroguanylin consumed a significantly higher ratio of demonstrated food (PR=0.76+/−0.04 SEM) compared to the novel-odored food (PR=0.49 +/−0.05 SEM). These same mice were retested one and four days after the initial day of testing. Even after repeated ingestion of warfarin, mice that had been exposed to uroguanylin still displayed a significant preference for the food containing warfarin and the demonstrated odor (Day 2: PR=0.72 +/−0.06; Day 5: PR=0.74 +/−0.08).

Uroguanylin-dependent preferences were found to be maintained over time. Mice form preferences to food and feeding sites when food odors are paired with the social cues uroguanylin. It was determined whether mice will maintain this preference and return to the learned food odor even after the food has been tainted with the commonly used rodenticide warfarin. Mice were allowed to explore saline containing a food odor (demonstrated odor) and with (black) or without (gray) 50 nM uroguanylin for 1 hr (FIG. 8). Mice were then given a choice of two powdered foods containing 0.025% warfarin plus either the demonstrated odor or a novel odor. The preference ratio (PR) is computed as: food with demonstrated odor (g) consumed/ total food (g) consumed. A preference ratio of 0.5 indicates no preference. Mice that had sampled the food odor with uroguanylin consumed a significantly higher ratio of demonstrated food (PR=0.76+/−0.04 SEM) compared to the novel-odored food (PR=0.49 +/− 0.05 SEM) (FIG. 8). These same mice were retested one and four days after the initial day of testing. Even after repeated ingestion of warfarin, mice that had been exposed to uroguanylin still displayed a significant preference for the food containing warfarin and the demonstrated odor (Day 2: PR=0.72 +/−0.06; Day 5: PR=0.74 +/−0.08). A two-way repeated measures ANOVA revealed a significant effect of uroguanylin on the preference ratio (F[1,46]=19.55, P<0.001). By contrast, there was no effect of the test day on the preference ratio. Tukey's post hoc analysis showed that uroguanylin-dependent preferences were significantly greater than those of mice demonstrated with saline alone on each of the test days (P<0.01).

Figure 9:
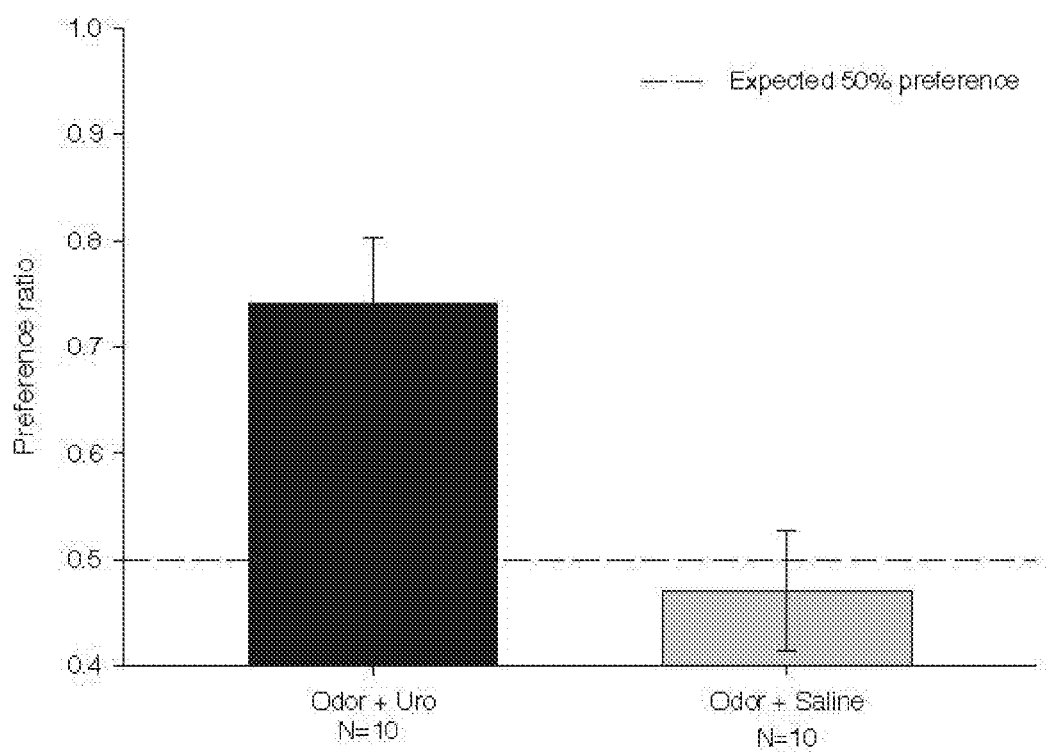
FIG. 9: Maintenance of preferences for foods containing warfarin. Mice exposed to 50 nM uroguanylin and a demonstrated odor showed a preference for food containing that demonstrated odor (not shown). On day 2, the same mice were given a choice of a powdered food containing 0.025% warfarin plus the demonstrated odor or powdered food contain another novel odor (different than that used on day 1) but no warfarin. Mice that had sampled uroguanylin in the initial exposure still significantly preferred the food containing the demonstrated odor and warfarin.

Maintenance over time of preferences for foods containing warfarin was also found. To test whether mice will maintain uroguanylin-dependent preferences for food containing warfarin even when an unadulterated food is present and is identified by a novel odor, a modified preference testing procedure was performed. Mice were allowed to explore saline containing a food odor (demonstrated odor)

and with (black) or without (gray) 50 nM uroguanylin for 1 hr (FIG. 9). Mice were then given a choice of two powdered foods containing 0.025% warfarin plus either the demonstrated odor or a novel odor. The preference ratio (PR) is computed as: food with demonstrated odor (g) consumed/ total food (g) consumed. A preference ratio of 0.5 indicates no preference. As seen in FIG. 6 and in Arakawa et al. (2013), mice exposed to uroguanylin and a demonstrated odor showed a preference for food containing that demonstrated odor. On day 2 (FIG. 9), the same mice were given a choice of a powdered food containing 0.025% warfarin plus the demonstrated odor or powdered food contain another novel odor (different than that used on day 1) but no warfarin. Mice that had sampled uroguanylin in the initial exposure still significantly preferred the food containing the demonstrated odor and warfarin (PR=0.74 +/−0.06 SEM; one-way ANOVA, (F [1,19]=10.1, P<0.005)).

The mammalian olfactory system responds to a diverse array of chemical stimuli including gases, volatiles, and even peptides and proteins. Many of these chemicals activate specialized olfactory subsystems and elicit specific behaviors or physiological changes (Munger et al. 2009). It was previously reported that uroguanylin activates a subpopulation of sensory cells, GC-D+ OSNs (Leinders-Zufall et al. 2007). Furthermore, it was found that GC-D+ OSNs mediate the acquisition of socially transmitted food preferences in response to the social stimulus $CS_2$ (Munger et al. 2010). Those findings are extended here to show that both feces and the GC-D agonist uroguanylin can promote the acquisition of food preferences.

Both feces and urine are rich sources of conspecific and heterospecific semiochemicals that can carry critical information about social or reproductive status or the presence of predators or competitors (Chamero et al. 2007; Papes et al. 2010; Roberts et al. 2010; Ferrero et al. 2011; Isogai et al. 2011). Furthermore, mice will reduce feeding in areas containing feces and urine of competitors (Dobly et al. 2001). GC-D+ OSNs respond to urine with an increase in intracellular $Ca^{2+}$ and action potential firing (Leinders-Zufall et al. 2007). Uroguanylin is produced in the intestine, where it can act locally to promote the absorption of electrolytes (Forte 2004; Seeley and Tschop 2011). Its function in the kidney is similar (Forte 2004; Seeley and Tschop 2011). Upon excretion in urine or feces, uroguanylin is available to act as a semiochemical for other animals that encounter fecal or urine deposits. The results presented here showing that feces contains cues that, when paired with a food odor, can promote the acquisition of food preferences is consistent with a role for uroguanylin as a chemosensory cue important for social learning in rodents.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

Arakawa, H., Zufall, F., Munger, S. D. (2013) The receptor guanylyl cyclase type D (GC-D) ligand uroguanylin promotes the acquisition of food preferences in mice. Chem Senses. 38: 391-397.

Bean N J, Galef B G, Jr., Mason J R. 1988. The effect of carbon disulphide on food consumption by house mice. J Wildl Manage 52: 502-507.

Chamero P, Marton T F, Logan D W, Flanagan K, Cruz J R, Saghatelian A, Cravatt B F, Stowers L. 2007. Identification of protein pheromones that promote aggressive behaviour. Nature 450: 899-902.

Crawley J N. 2007. Mouse behavioral assays relevant to the symptoms of autism. Brain Pathol 17: 448-459.

Dobly A, Rozenfeld F M, Haim A. 2001. Effect of congeneric chemical signals of different ages on foraging response and food choice in the field by golden spiny mice (Acomys russatus). J Chem Ecol 27: 1953-1961.

Ferrero D M, Lemon J K, Fluegge D, Pashkovski S L, Korzan W J, Datta S R, Spehr M, Fendt M, Liberles S D. 2011. Detection and avoidance of a carnivore odor by prey. Proc Natl Acad Sci USA 108: 11235-11240.

Forte L R, Jr. 2004. Uroguanylin and guanylin peptides: pharmacology and experimental therapeutics. Pharmacol Ther 104: 137-162.

Galef B G. 2012. A case study in behavioral analysis, synthesis and attention to detail: social learning of food preferences. Behav Brain Res 231: 266-271.

Galef B G, Jr. 1985. Direct and indirect behavioral pathways to the social transmission of food avoidance. Ann NY Acad Sci 443: 203-215.

Galef B G, Jr., Heiber L. 1976. Role of residual olfactory cues in the determination of feeding site selection and exploration patterns of domestic rats. J Comp Physiol Psychol 90: 727-739.

Galef B G, Jr., Kennett DJ. 1987. Different mechanisms for social transmission of diet preference in rat pups of different ages. Devel Psychobiol 20: 209-215.

Galef B G, Jr., Mason J R, Preti G, Bean N J. 1988. Carbon disulfide: a semiochemical mediating socially-induced diet choice in rats. Physiol Behav 42: 119-124.

Galef B G, Jr., Wigmore S W, Kennett D J. 1983. A failure to find socially mediated taste aversion learning in Norway rats (R. norvegicus). J Comp Psychol 97: 358-363.

Isogai Y, Si S, Pont-Lezica L, Tan T, Kapoor V, Murthy V N, Dulac C. 2011. Molecular organization of vomeronasal chemoreception. Nature 478: 241-245.

Laland K N, Plotkin H C. 1991. Excretory deposits surrounding food sites facilitate social learning of food preferences in Norway rats. Anim Behav 41: 997-1005.

Laland K N, Plotkin H C. 1993. Social transmission of food preferences among Norway rats by marking of food sites and by gustatory contact. Anim Learn Behav 21: 35-41.

Leinders-Zufall T, Cockerham R E, Michalakis S, Biel M, Garbers D L, Reed R R, Zufall F, Munger S D. 2007. Contribution of the receptor guanylyl cyclase GC-D to chemosensory function in the olfactory epithelium. Proc Natl Acad Sci USA 104: 14507-14512.

Munger S D, Leinders-Zufall T, McDougall L M, Cockerham R E, Schmid A, Wandernoth P, Wennemuth G, Biel M, Zufall F, Kelliher K R. 2010. An olfactory subsystem that detects carbon disulfide and mediates food-related social learning. Curr Biol 20: 1438-1444.

Munger S D, Leinders-Zufall T, Zufall F. 2009. Subsystem organization of the mammalian sense of smell. Annu Rev Physiol 71: 115-140.

Papes F, Logan D W, Stowers L. 2010. The vomeronasal organ mediates interspecies defensive behaviors through detection of protein pheromone homologs. Cell 141: 692-703.

Pastro L A, Banks B P. 2006. Foraging responses of wild house mice to accumulations of conspecific odor as a predation risk. Behav. Ecol. Sociobiol. 60: 101-107.

Posadas-Andrews A, Roper T J. 1983. Social transmission of food preference in adult rats. Anim Behav 31: 265-271.

Roberts S A, Simpson D M, Armstrong S D, Davidson A J, Robertson D H, McLean L, Beynon R J, Hurst J L. 2010. Darcin: a male pheromone that stimulates female memory and sexual attraction to an individual male's odour. BMC Biol 8: 75.

Ryan B C, Young N B, Moy S S, Crawley J N. 2008. Olfactory cues are sufficient to elicit social approach behaviors but not social transmission of food preference in C57BL/6J mice. Behav Brain Res 193: 235-242.

Seeley R J, Tschop M H. 2011. Uroguanylin: how the gut got another satiety hormone. The J Clin Invest 121: 3384-3386.

Valentino M A, Lin J E, Snook A E, Li P, Kim G W, Marszalowicz G, Magee M S, Hyslop T, Schulz S, Waldman S A. 2011. A uroguanylin-GUCY2C endocrine axis regulates feeding in mice. J Clin Invest 121: 3578-3588.

Valsecchi P, Galef B G, Jr. 1989. Social influences of the food preferences of house mice (Mus musculus). Int J Comp Psychol 2: 245-256.

What is claimed is:

1. A method for rodent control, comprising:
   (a) inducing a food or odor preference in a rodent by exposing a rodent to a training composition comprising (i) matter having an odor, and (ii) a guanylin family peptide or variant thereof, and
   (b) administering to the rodent an edible composition comprising (i) the odor of the training composition and (ii) a rodent control agent, thereby controlling a rodent.

2. The method of claim 1, wherein the rodent is a rat or mouse.

3. The method of claim 1, wherein the rodent control agent is a poison and the control is death of the rodent.

4. The method of claim 1, wherein the training composition is a saline solution comprising (i) matter having an odor and (ii) between about 1 nM and 50 µM guanylin family peptide.

5. The method of claim 1, wherein the guanylin family peptide is guanylin or uroguanylin or a variant thereof.

6. The method of claim 1, wherein the guanylin family peptide is rat guanylin, rat uroguanylin, mouse guanylin, mouse uroguanylin, or a variant thereof.

7. The method of claim 1, wherein the training composition and the edible composition are located in separate compartments of a bait station.

8. A method for reducing a population of rodents, comprising:
(a) inducing a food or odor preference in a population of rodents by exposing a population of rodents to a training composition comprising (i) matter having an odor and (ii) a guanylin family peptide or variant thereof, and
(b) administering to the population of rodents an edible composition comprising (i) the odor of the training composition and (ii) a rodent control agent, thereby reducing a population of rodents.

9. The method of claim 8, wherein the rodent is a rat or mouse.

10. The method of claim 8, wherein the rodent control agent is a poison and the control is death of the rodent.

11. The method of claim 8, wherein the training composition is a saline solution comprising (i) matter having an odor and (ii) between about 1 nM and 50 µM guanylin family peptide.

12. The method of claim 8, wherein the guanylin family peptide is guanylin or uroguanylin or a variant thereof.

13. The method of claim 8, wherein the guanylin family peptide is rat guanylin, rat uroguanylin, mouse guanylin, mouse uroguanylin, or a variant thereof.

14. The method of claim 8, wherein the training composition and the edible composition are located in separate compartments of a bait station.

15. A method for rodent control, comprising providing a complete composition to a rodent comprising (i) an odor, (ii) a guanylin family peptide or variant thereof, and (iii) an ingestible matter comprising a rodent control agent, thereby controlling a rodent.

16. The method of claim 15, wherein the odor and the guanylin family peptide induce a food or odor preference in the rodent.

17. The method of claim 15, wherein the rodent is a rat or mouse.

18. The method of claim 15, wherein the rodent control agent is a poison and the control is death of the rodent.

19. The method of claim 15, wherein the complete composition comprises between about 1 nM and 50 µM guanylin family peptide.

20. The method of claim 15, wherein the guanylin family peptide is guanylin or uroguanylin or a variant thereof.

21. The method of claim 15, wherein the guanylin family peptide is rat guanylin, rat uroguanylin, mouse guanylin, mouse uroguanylin, or a variant thereof.

22. A method for reducing a population of rodents, comprising providing a complete composition to a population of rodents comprising (i) an odor, (ii) a guanylin family peptide or variant thereof, and (iii) an ingestible matter comprising a rodent control agent, thereby controlling a rodent.

23. The method of claim 22, wherein the odor and the guanylin family peptide induce a food or odor preference in the rodent.

24. The method of claim 22, wherein the rodent is a rat or mouse.

25. The method of claim 22, wherein the rodent control agent is a poison and the control is death of the rodent.

26. The method of claim 22, wherein the complete composition comprises between about 1 nM and 50 µM guanylin family peptide.

27. The method of claim 22, wherein the guanylin family peptide is guanylin or uroguanylin or a variant thereof.

28. The method of claim 22, wherein the guanylin family peptide is rat guanylin, rat uroguanylin, mouse guanylin, mouse uroguanylin, or a variant thereof.

* * * * *